United States Patent
Dahl

(10) Patent No.: US 6,343,612 B1
(45) Date of Patent: Feb. 5, 2002

(54) PORTABLE PACIFIER CLEANER AND CONTAINER

(76) Inventor: Carla Cherry Dahl, 255 Oakwood Rd., Hopkins, MN (US) 55343

(*) Notice: Subject to any disclaimer, the term of this patent is extended or adjusted under 35 U.S.C. 154(b) by 0 days.

(21) Appl. No.: 09/479,573

(22) Filed: Jan. 7, 2000

Related U.S. Application Data

(60) Provisional application No. 60/115,930, filed on Jan. 14, 1999.

(51) Int. Cl.$^7$ ................................................ B08D 3/04
(52) U.S. Cl. ....................... 134/117; 134/135; 134/201
(58) Field of Search ................................ 134/200, 201, 134/135, 117, 901; 206/205, 83, 5.1, 428; D32/40, 43, 45, 53; D4/129, 199

(56) References Cited

U.S. PATENT DOCUMENTS

| | | | | |
|---|---|---|---|---|
| 2,135,503 A | * | 11/1938 | Guntrip | |
| 2,163,862 A | * | 6/1939 | Wing | |
| 2,565,899 A | * | 8/1951 | Wilcox | |
| 2,664,854 A | * | 1/1954 | Talbot | |
| 3,035,589 A | * | 5/1962 | King | |
| 3,101,087 A | * | 8/1963 | Watson | |
| 3,167,079 A | * | 1/1965 | Weil | |
| 3,280,828 A | * | 10/1966 | Stiel | |
| 3,804,236 A | * | 4/1974 | Tanaka | |
| 3,894,551 A | * | 7/1975 | Stohlman | |
| 4,049,165 A | * | 9/1977 | Goldhaft | |
| 4,054,220 A | * | 10/1977 | Rosenstein | |
| 4,337,858 A | * | 7/1982 | Thomas et al. | |
| 5,167,232 A | * | 12/1992 | Ohta et al. | |
| 5,211,656 A | * | 5/1993 | Maddocks et al. | |
| 5,402,810 A | | 4/1995 | Donley | ........................ 134/135 |
| 5,423,419 A | * | 6/1995 | Wentz et al. | |
| 5,425,196 A | * | 6/1995 | Schwarze | |
| 5,839,457 A | * | 11/1998 | Rijken et al. | |

* cited by examiner

Primary Examiner—Frankie L. Stinson
(74) Attorney, Agent, or Firm—Kinney & Lange, P.A.

(57) ABSTRACT

An apparatus for cleaning and storing pacifiers, comprising an essentially cylindrical body containing two compartments, the first being vertically disposed above the second. The first compartment is designed for cleaning a pacifier and has a water-tight, screw-on lid. The lid contains a channel for accommodating a strap which is used to conveniently attach the apparatus to a baby stroller or other location. The second compartment has a snap-on lid and is designed for the sanitary transportation of a spare pacifier.

14 Claims, 3 Drawing Sheets

PORTABLE PACIFIER CLEANER AND CONTAINER

CROSS-REFERENCE TO RELATED APPLICATION(S)

This application claims the priority benefits of U.S. Provisional patent application Ser. No. 60/115,930, filed Jan. 14, 1999.

BACKGROUND OF THE INVENTION

This invention relates to a portable pacifier container with a dual purpose of cleaning a pacifier and sanitarily transporting a spare pacifier.

Parents commonly use pacifiers to quiet and soothe crying infants. Because a pacifier is held in a child's mouth, it is particularly important that the pacifier is clean and germ-free. However, because an infant often allows a pacifier to fall out of its mouth, pacifiers are easily and frequently soiled. Unfortunately, when the infant is away from home or other readily-available sources of running water, it is often difficult for the parent to clean the soiled pacifier. Thus, an apparatus which allows a parent to clean a pacifier "on the go" offers great utility.

It is also important for parents to keep their child's pacifiers clean during transport. However, many parents just put the pacifier into an unsanitized pocket, diaper bag, purse, or the like. Not only does the pacifier have the potential of becoming soiled, it is often difficult for the parent to find and retrieve. Thus, there is a need not only for a portable cleaning apparatus but also for a container that will keep the pacifier clean and handy.

BRIEF SUMMARY OF THE INVENTION

The present invention is a portable apparatus which serves two primary functions: cleaning a soiled pacifier and hygienically and conveniently storing a clean pacifier for transport in a manner that allows for easy accessibility. In a preferred embodiment, the present invention comprises a container with two interior compartments: a wet cleaning chamber or compartment and a dry storage chamber or compartment.

The top compartment has a waterproof, screw-on top lid which allows the compartment to hold water or other pacifier rinsing fluid. The top lid also has a channel for holding a strap that can secure the apparatus to a stroller, infant car seat, diaper bag, or purse, for example, thereby keeping the apparatus conveniently accessible. In a preferred embodiment, the bottom compartment offers room to hold a spare pacifier and has a snap-on lid.

DETAILED DESCRIPTION

Figure 1:
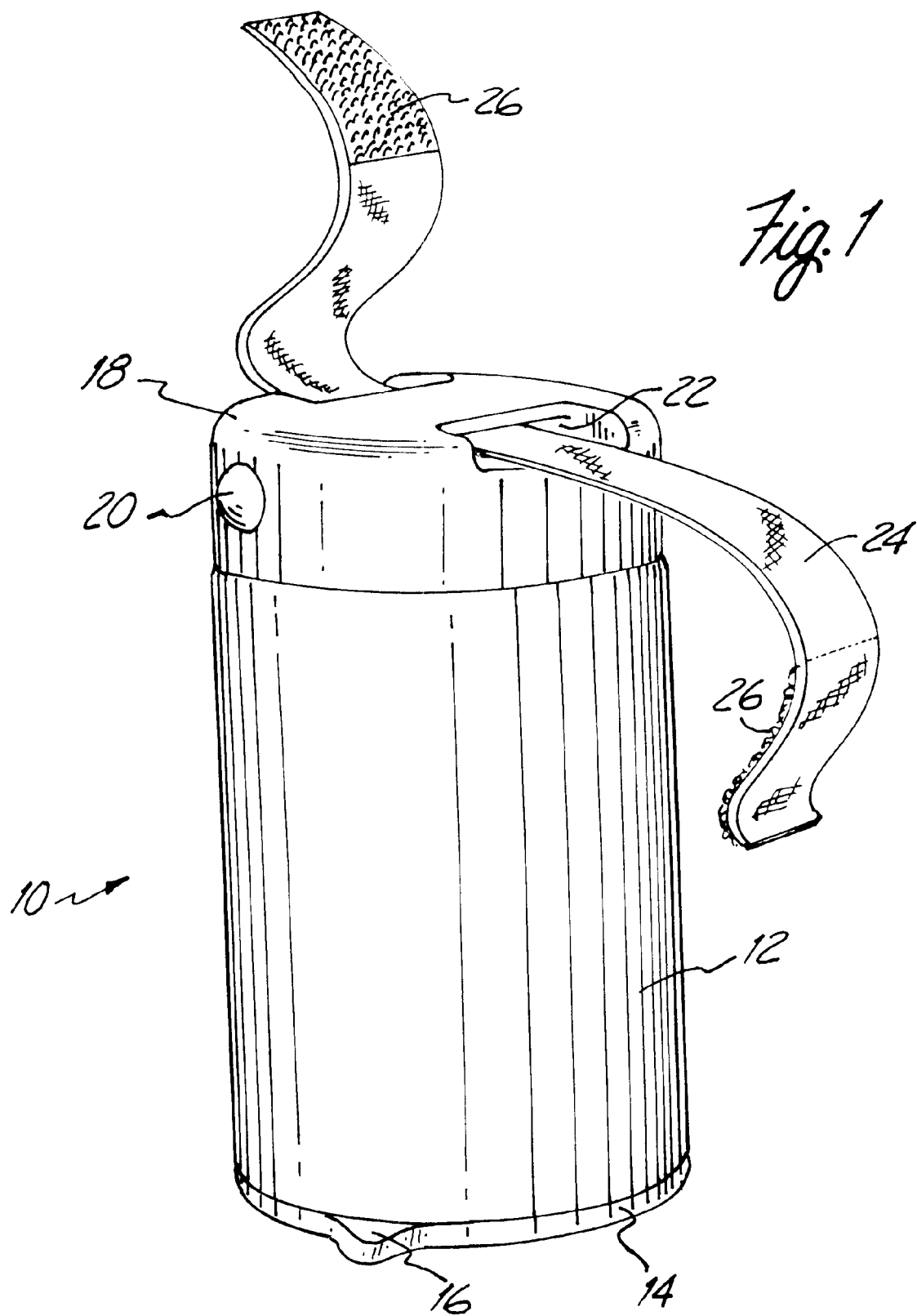
FIG. 1 is a perspective view of the exterior of a portable pacifier cleaner and container embodying the present invention.

FIG. 1 shows a portable pacifier cleaner and container 10 embodying the present invention. In a preferred embodiment, the invention includes essentially cylindrical body 12, bottom lid 14 with opening protrusion 16, top lid 18 with turning protrusion 20 and strap channel 22, and strap 24 secured by hook-and-loop fastener ("velcro") tabs 26.

The apparatus can be constructed of any material, but plastic is preferred for its light weight and resistance against breakage. In a preferred embodiment, cylindrical body 12, top lid 18 and bottom lid 14 may be manufactured of plastic by an injection molding process. Alternatively, parts may be made of a different material, such as rubber. In particular, bottom lid 14 can be made of rubber or a relatively soft polymeric material so that it is easier to use, is more resistant to breakage, and forms a better seal.

In a preferred embodiment, cylindrical body 12 is about 4 inches high and about 2½ inches in diameter. Top lid 18 is preferably secured to cylindrical body 12 by a threaded connection between cylindrical body 12 and top lid 18, and bottom lid 14 is a snap-on lid. However, any alternative means known in the art may be used for removably securing lids 18 and 14 to cylindrical body 12, such as by the use of hinges, buttons, hooks, or other fasteners. Top lid 18 and bottom lid 14 can also be attached to cylindrical body 12 so that they will not be lost when disengaged from cylindrical body 12.

Protrusion 20 may be disposed on top lid 18 to assist a user in twisting top lid 18 off cylindrical body 12. Similarly, protrusion 16 may be disposed in bottom lid 14 to assist a user in separating bottom lid 14 from cylindrical body 12. In a preferred embodiment, integrated strap channel 22, approximately one inch wide, is disposed in top lid 18. However, strap 24 is optional and may be secured to cylindrical body 12 or top lid 18 in any known manner. In a preferred embodiment, strap 24 comprises an approximately 1 inch wide and 10 inch long strip of webbing made of nylon, propylene, or other textile material with hook and loop fasteners on the ends. However, strap 24 may be made of any material and may be of any dimension. Additionally, any known fastener may be used, such as snaps, hooks, or buttons; or the ends of strap 24 may be simply tied together.

Use of a strap allows the apparatus to be secured to a stroller, infant car seat, diaper bag, purse, or other convenient location. It allows the apparatus to remain easily accessible at all times. Without such an attachment mechanism, a pacifier container might be easily lost, or otherwise difficult to find among other infant items. While prior art products for cleaning pacifiers may be portable in size, none offer the convenience of the present invention, which offers three primary advantages: 1) a wet compartment for cleaning a pacifier, 2) a dry compartment for transporting a spare pacifier, and 3) a carrying strap which allows the apparatus to be easily within a parent's view and reach at all times.

While the preferred embodiment is described with a "wet" compartment on the top and a "dry" compartment on the bottom, variations in the configurations of the compartments within the contemplation of those skilled in the art are considered to be within the scope of the invention. The wet and dry compartments function independently. Unlike prior art products, the cleaning function of the apparatus (in the wet compartment) is physically separated from the storage function (in the dry compartment).

Figure 2:
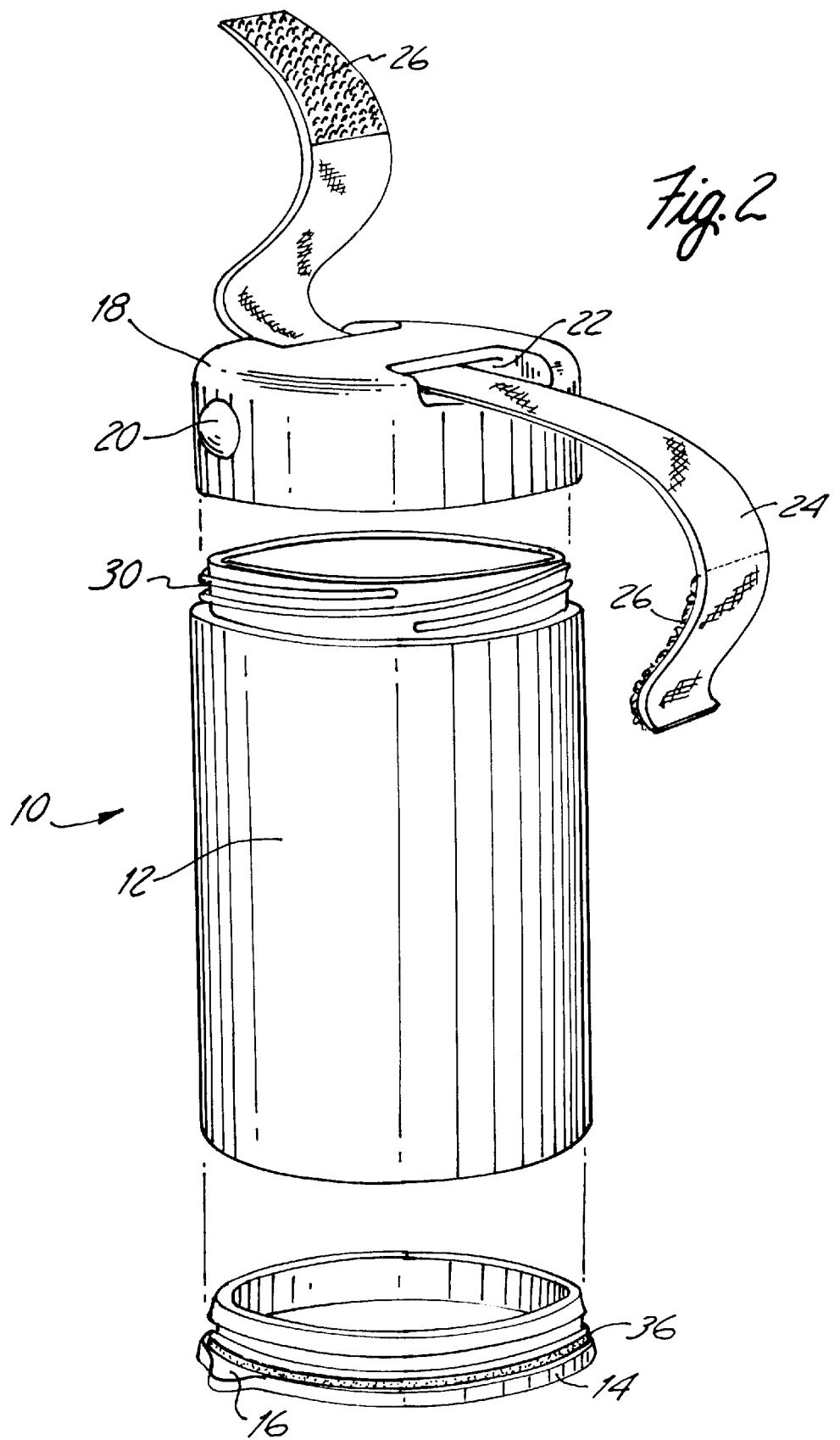
FIG. 2 is a perspective view of the exterior of a portable pacifier cleaner and container of the present invention with the top lid and the bottom lid removed.

FIG. 2 shows a preferred embodiment of portable pacifier cleaner and container 10 with top lid 18 and bottom lid 14 removed. As in FIG. 1, FIG. 2 shows essentially cylindrical body 12, bottom lid 14 with opening protrusion 16, top lid 18 with turning protrusion 20 and strap channel 22, and strap 24 secured by hook-and-loop fastener tabs 26. Additionally, FIG. 2 shows external screw threads 30 on cylindrical body 12 and circumferential groove 36 on bottom lid 14.

In a preferred embodiment, internal screw threads 28 in top lid 18 (shown in FIG. 3) mate with external screw threads 30 on cylindrical body 12, allowing top lid 18 to be screwed onto cylindrical body 12. Either top lid 18 or cylindrical body 12 may contain an o-ring 32 (shown in FIG. 3) to facilitate a watertight seal. In a preferred embodiment, bottom lid 14 snaps into place and is held in contact with cylindrical body 12 by the mating of a circumferential ridge 34 (shown in FIG. 3) along a lower inside edge of cylindrical body 12 with a circumferential groove 36 on bottom lid 14.

One advantage of apparatus 10 is that it is completely washable. Strap 24 can be removed and easily cleaned by hand or in a clothes washing machine. Pacifier cleaner and container 10 can be disassembled for cleaning by hand or in an automatic dishwasher, and can therefore be sterilized after each use.

Figure 3:
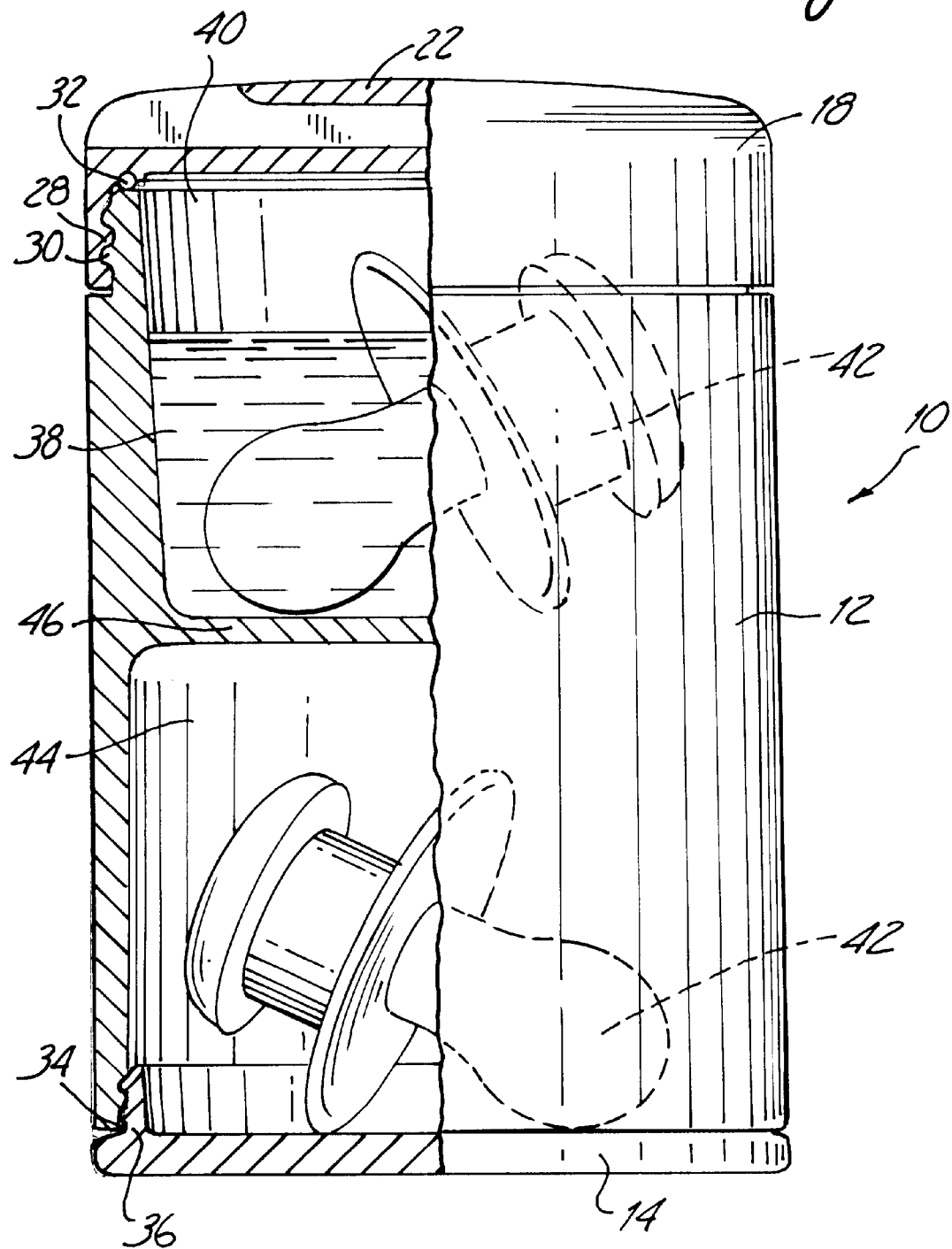
FIG. 3 is a partial sectional view of a portable pacifier cleaner and container of the present invention, showing a cleaning fluid in the top compartment and pacifiers in the top wet compartment and the bottom dry compartment.

FIG. 3 shows a partial cross sectional view of a portable pacifier cleaner and container 10 according to the present invention, showing a cleaning fluid 38 in top compartment 40 and pacifiers 42 in each of top compartment 40 and bottom compartment 44. FIG. 3 additionally shows essentially cylindrical body 12, bottom lid 14, top lid 18 with strap channel 22, internal screw threads 28, external screw threads 30, o-ring 32, circumferential ridge 34, circumferential groove 36, and partition 46.

Fixed, solid partition 46 in the approximate center of cylindrical body 12 divides cylindrical body 12 into two compartments: wet top compartment 40 and dry bottom compartment 44. As shown, wet compartment 40 has o-ring 32 which helps to seal top lid 18 to cylindrical body 12, rendering wet top compartment 40 watertight.

While the apparatus is not designed to thoroughly sanitize a pacifier, it is helpful for rinsing the pacifier when no source of running water or other cleaning method is available. A soiled pacifier is simply placed into fluid 38 of top compartment 40, top lid 18 is secured to cylindrical body 12, and apparatus 10 is shaken gently to rinse the pacifier. The present invention offers a convenient means to clean a pacifier which is much more effective than alternative means such as wiping it on clothes or swabbing it with a diaper wipe and thereby leaving a distasteful chemical residue. A pacifier should not be stored in the liquid because prolonged submersion may adversely affect the silicone material used in many pacifiers.

Pacifier cleaning fluid 38 is preferably water but it may also be a very mild soap or other non-toxic cleaning solution. One advantage of the present invention is that cleaning solution 38 can be easily replaced when a water source does become available. Even where a water source is available, the apparatus of the present invention offers utility in that wet compartment 40 can hold a stronger cleaning fluid 38 for more thorough cleaning. After a pacifier is cleaned in fluid 38, it can be rinsed with clear water before being given to a child or stored in dry compartment 44.

While the principles of this invention have been described in connection with specific embodiments, it should be understood clearly that these descriptions are made only by way of example and are not intended to limit the scope of the invention. Workers skilled in the art will recognize that changes may be made in form and detail without departing from the spirit and scope of the invention.

What is claimed is:

1. A portable apparatus for cleaning and storing pacifiers, the apparatus comprising:
   a housing; and
   a fixed, horizontal, solid, and imperforated partition dividing the housing into a first compartment and a second compartment,
   wherein the first compartment is adapted to contain a pacifier and a cleaning fluid, and
   wherein the second compartment is adapted to contain a pacifier.

2. The apparatus of claim 1, wherein the apparatus is made of plastic.

3. The apparatus of claim 1, wherein:
   the housing has an essentially cylindrical body, and
   wherein the first compartment is vertically disposed above the second compartment.

4. The apparatus of claim 3, wherein the essentially cylindrical body is about 4 inches high and about 2.5 inches in diameter.

5. The apparatus of claim 3, further comprising:
   a top lid which encloses the first compartment and is removably secured to the first compartment; and
   a bottom lid which encloses the second compartment and is removably secured to the second compartment.

6. The apparatus of claim 5, wherein the cylindrical body and top lid are made of plastic; and
   the bottom lid is made of a polymeric material.

7. The apparatus of claim 5, further comprising:
   a channel in the top lid for receiving a strap, wherein the channel is about 1 inch wide.

8. The apparatus of claim 7, wherein the strap comprises a textile material about 1 inch wide and about 10 inches long, the strap having first and seconds ends which are secured together, wherein the first and second ends are secured by hook-and-loop fastening tabs.

9. The apparatus of claim 5, wherein:
   the top lid has internal screw threads, and
   the cylindrical body has external screw threads,
   such that the threads of the top lid mate with the threads of the cylindrical body, thereby removably securing the top lid to the cylindrical body.

10. The apparatus of claim 9, further comprising a watertight seal between the top lid and the cylindrical body.

11. The apparatus of claim 10, further comprising an o-ring between the top lid and the cylindrical body to provide the watertight seal therebetween.

12. The apparatus of claim 9, wherein the top lid further comprises:
   a protrusion for facilitating the turning of the top lid with respect to the cylindrical body.

13. The apparatus of claim 5, wherein:
   the bottom lid has a circumferential groove, and
   the cylindrical body has a circumferential ridge,
   such that the groove mates with the ridge, thereby removably securing the bottom lid to the cylindrical body.

14. The apparatus of claim 12 wherein the bottom lid further comprises:
   a protrusion for facilitating separation of the bottom lid from the cylindrical body.

* * * * *